United States Patent [19]

Remes et al.

[11] Patent Number: 5,706,801
[45] Date of Patent: Jan. 13, 1998

[54] SENSING AND COMMUNICATIONS SYSTEM FOR USE WITH OXYGEN DELIVERY APPARATUS

[75] Inventors: Scott Remes, Burnsville, Minn.; Larry Heyl, Morrison, Colo.; Dick Middleton, Bloomington, Minn.

[73] Assignee: Caire Inc., Burnsville, Minn.

[21] Appl. No.: 508,980

[22] Filed: Jul. 28, 1995

[51] Int. Cl.$^6$ ........................... A61M 16/00
[52] U.S. Cl. ............... 128/202.26; 128/202.22; 128/204.18; 128/204.21; 128/204.22; 128/204.23; 128/205.11; 128/205.23
[58] Field of Search .......... 128/200.24, 202.12, 128/202.22, 202.26, 204.18, 204.21, 204.22, 204.23, 204.25, 204.29, 205.11, 205.12, 205.23, 205.27, 716, 719

[56] References Cited

U.S. PATENT DOCUMENTS

| | | | |
|---|---|---|---|
| 3,726,270 | 4/1973 | Griffis et al. | 128/2.08 |
| 4,516,424 | 5/1985 | Rowland | 73/23 |
| 4,561,287 | 12/1985 | Rowland | 73/213 |
| 4,627,860 | 12/1986 | Rowland | 55/162 |
| 4,838,275 | 6/1989 | Lee | 128/670 |
| 4,933,873 | 6/1990 | Kaufman et al. | 364/513.5 |
| 4,938,212 | 7/1990 | Snook et al. | 128/205.24 |
| 5,036,852 | 8/1991 | Leishman | 128/630 |
| 5,142,484 | 8/1992 | Kaufman et al. | 222/638 |
| 5,151,166 | 9/1992 | Harral et al. | 204/425 |
| 5,275,159 | 1/1994 | Griebel | 128/633 |
| 5,367,555 | 11/1994 | Isoyama | 379/38 |
| 5,390,238 | 2/1995 | Kirk et al. | 379/93 |
| 5,402,665 | 4/1995 | Hart et al. | 73/16 |
| 5,469,372 | 11/1995 | McBrearty et al. | 364/550 |
| 5,485,850 | 1/1996 | Dietz | 128/716 |
| 5,495,848 | 3/1996 | Aylsworth et al. | 128/207.18 |
| 5,540,220 | 7/1996 | Gropper et al. | 128/204.23 |
| 5,558,086 | 9/1996 | Smith et al. | 128/204.26 |

*Primary Examiner*—Vincent Millin
*Assistant Examiner*—William J. Deane, Jr.
*Attorney, Agent, or Firm*—Dorsey & Whitney LLP

[57] ABSTRACT

An oxygen delivery apparatus is used to supply oxygen-enriched air to a patient via a diffuser. A communication module containing an in-line flowmeter and oxygen concentration sensor is provided to measure the flow rate and oxygen concentration of the oxygen-enriched supplied to the patient. The length of a therapy session is also measured. The measured information is stored and periodically transmitted via a communication module including an internal modem to a remote computer system. The remote computer system includes a program that manipulates and stores the data transmitted from the module. Analysis of the data reveals the operational status of the oxygen delivery apparatus and whether the patient is complying with a prescribed regimen of use. The communication modules for a number of users in a given geographic can be monitored for efficient servicing.

41 Claims, 5 Drawing Sheets

| SER. NO. | DATE | NO. OF SESSIONS | SESSION START TIME | TAC |
|---|---|---|---|---|
| LOW CONC. | HIGH CONC. | AVG. CONC. | LOW FLOW | HIGH FLOW |
| AVG. FLOW | SESSION STOP TIME | • • • • • • • • • • • • | | CHECK |

SENSING AND COMMUNICATIONS SYSTEM FOR USE WITH OXYGEN DELIVERY APPARATUS

BACKGROUND OF THE INVENTION

The present invention generally relates to oxygen delivery apparatus including oxygen concentrators and liquid and compressed oxygen systems for supplying oxygen-enriched gas to a patient and, more particularly, to a sensing and communications system to be used therewith for periodic reporting of apparatus performance and information regarding patient compliance with a prescribed regimen of use.

An oxygen delivery apparatus is used to supply oxygen-enriched breathable air to a patient via a diffuser such as a cannula. The more popular form of oxygen delivery apparatus is an oxygen concentrator which typically includes a plurality of sieve beds which are used to remove nitrogen from atmospheric air. When properly functioning, typical sieve beds adsorb the majority of nitrogen supplied to the concentrator. An enriched gas containing from 80 to 95 percent oxygen is then supplied to a patient.

Health care providers often prescribe that a patient use an oxygen delivery apparatus as a treatment for respiratory distress. In particular, a patient has a prescribed regimen to breathe a given flow rate of oxygen-enriched air to compensate for a disproportionately low oxygen concentration in the patient's blood. However, patients do not always follow through with a prescribed treatment often resulting in less then satisfactory results. In addition to patient non-compliance, the operational performance of an oxygen delivery apparatus may degrade over time such that the air supplied to the patient contains less than the desired amount of oxygen.

It is known in the art to monitor medical equipment and to transmit an alarm to a location remote from the equipment. For example, U.S. Pat. No. 5,036,852 to Leishman discloses a method and apparatus for monitoring medical equipment. In the Leishman patent, if the equipment indicates a fault condition, this condition is promptly transmitted over a telephone line to a remote computer. The remote computer periodically interrogates the communication device so that all of the information contained therein can be printed and placed in the patient's file folder.

U.S. Pat. No. 4,627,860 to Rowland discloses an oxygen concentrator and test apparatus including a controller for monitoring or sensing functions and performance of various components of the concentrator. A portable testing apparatus may be connected to the controller so that the monitored functions of the concentrator can be visually displayed. The concentrator can be provided with a microprocessor means to signal a modem to dial a remote test apparatus when a problem or malfunction occurs with the concentrator.

These types of monitoring systems are adequate for their intended uses. However, neither permits the operational status of the oxygen delivery system to be effectively determined or whether a patient is complying with a prescribed regimen of use. Additionally, neither monitoring system is a stand-alone device because each depends upon sensors built-in to the medical equipment being monitored.

SUMMARY OF THE INVENTION

In the sensing and communication system of the present invention, an oxygen delivery apparatus is used to supply oxygen-enriched air to a patient via a diffuser. An in-line flowmeter and oxygen concentration sensor are provided so that the flow rate and oxygen concentration of the oxygen-enriched supplied to the patient can be periodically determined. The length of a therapy session is also monitored. If desired, a blood oximeter also can be connected to the system so that blood gas information can be monitored. The information collected is, preferably, stored and periodically transmitted via a communication module including an internal modem to a remote computer system. In the event of equipment failure, the remote computer may be immediately notified.

The communication modules for a number of users in a given geographic area can be monitored for efficient servicing. The remote computer system includes a program that manipulates, stores and displays the data transmitted from each of the modules. Analysis of the data reveals the operational status of each oxygen delivery apparatus and whether a patient is complying with a prescribed regimen of use. The problems associated with and the risk of catastrophic failure are minimized because proper data analysis permits the determination of whether an oxygen delivery apparatus is trending into a failure mode.

DETAILED DESCRIPTION OF THE INVENTION

Figure 1:
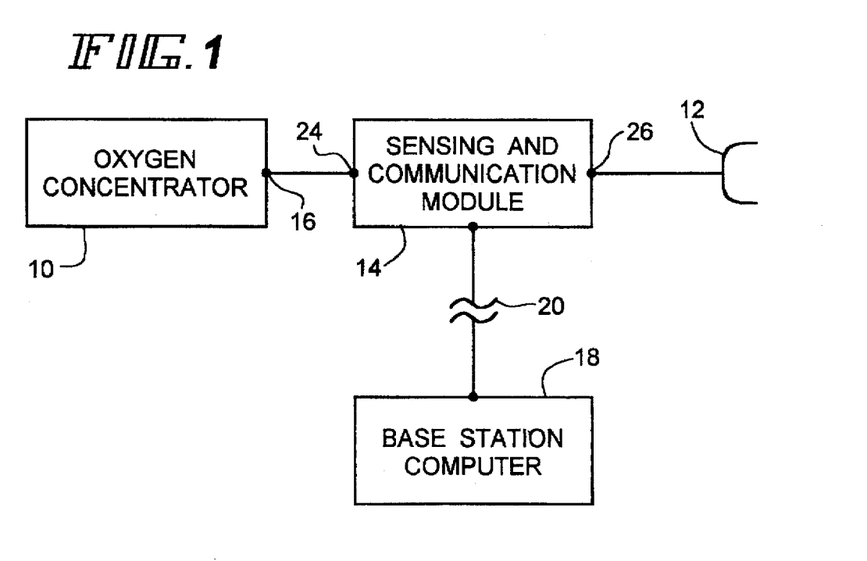
FIG. 1 is a block diagram illustrating the operation of the sensing and communications module of the invention.

Referring to FIG. 1, a block diagram illustrating the use of the sensing and communications system of the present invention is illustrated. An oxygen concentrator 10 is illustrated for supplying oxygen-enriched air to a patient through a diffuser 12 (typically a cannula). Equally suitable for use with the present invention are liquid oxygen and compressed oxygen dispensing devices. A compact sensing and communications module 14 is connected between the outlet 16 of concentrator 10 and diffuser 12. Module 14 permits the periodic transmission of flow rate and oxygen concentration data to a remote computer 18 over a phone line 20 as discussed hereafter.

Figure 2:
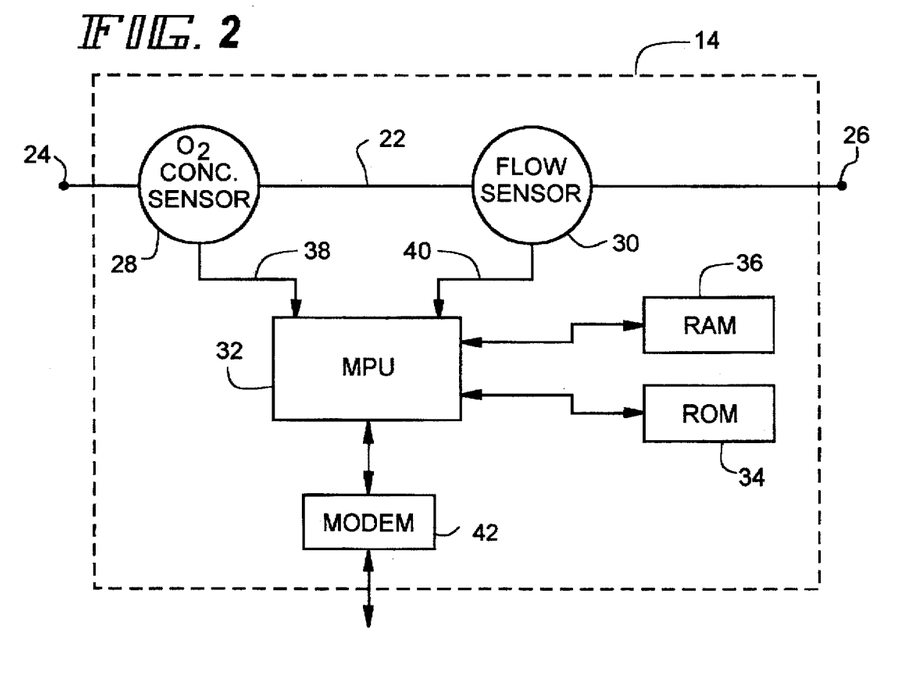
FIG. 2 is a block diagram of the module of FIG. 1.

FIG. 2 is a block diagram of the internal components of sensing and communications module 14. Module 14 includes an oxygen-enriched air line 22 having an input 24 connected to output 16 of concentrator 10 and an output 26 connected to diffuser 12. An in-line oxygen concentration sensor 28 and an in-line flow sensor 30 generate electrical signals that are proportional to the concentration of oxygen and the flow rate of oxygen-enriched air in air line 22, respectively. Preferably, concentration sensor 28 is ultrasonic and is capable of sensing oxygen concentrations from twenty to one hundred percent ambient. Such devices are available from Douglas Scientific of Kansas City, Kans., for example, Oxy Alert Model MK 8-D. Flow sensor 30 is preferably a differential pressure device which measures the pressure drop across a fixed orifice and is capable of sensing flow rates from zero to six liters per minute. Alternatively, heated thermistors or hot wire aniometers can be used to measure flow.

Figure 2A:
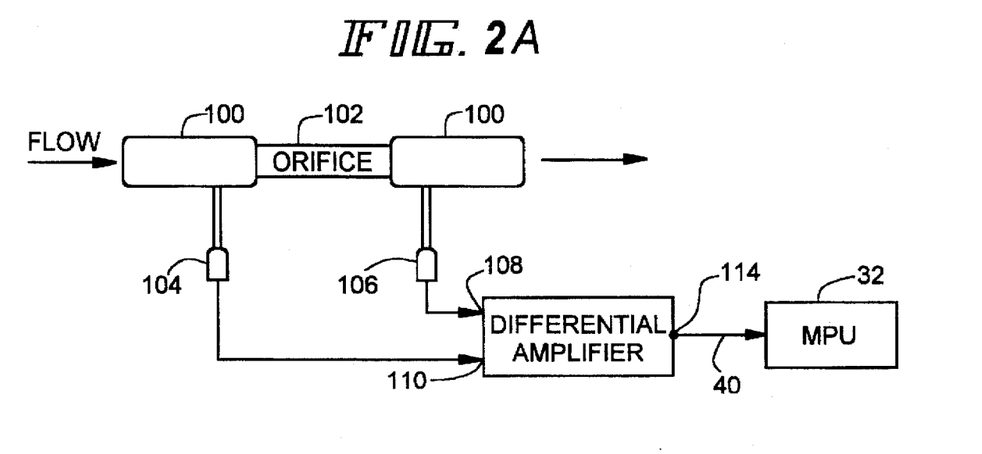
FIG. 2A is a schematic diagram of the flow rate sensor shown in FIG 2.

FIG. 2A is a schematic diagram illustrating the operation of flow sensor 30 which includes a conduit 100 having a restricted orifice 102 in circuit with line 22 (FIG. 2). The flow rate of the oxygen-enriched gas in conduit 100 is measured indirectly by sensing the pressure drop across orifice 102. For this purpose, two pressure sensors 104 and 106, each of which produces an output voltage related to a sensed pressure, are provided on the upstream and downstream side of restricted orifice 104, respectively. A pressure sensor suitable for use with the present invention is ICSensors model 1210.

The output voltages from pressure sensors 104 and 106 are electrically connected to the inputs 108 and 110 of differential amplifier 112. Differential amplifier 112 generates a voltage at its output 114 which is related to the difference of the voltages at its inputs 108 and 110 as is well known in the art. The voltage at output 114 is substantially related to the flow rate of the oxygen-enriched air in line 22 and is delivered to the microprocessor 32 over line 40.

Figure 2B:
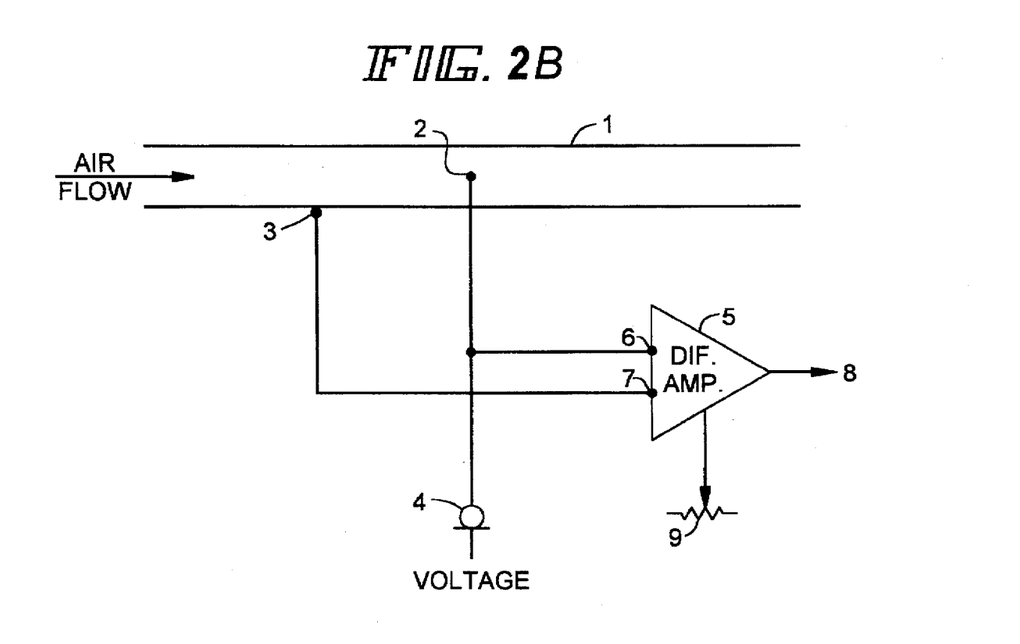
FIG. 2B is a schematic diagram of a heated thermistor flow sensor.

FIG. 2B is a schematic diagram of a heated thermistor flow sensor. A constant current source 4 supplies a fixed current to thermistor 2 positioned in a conduit 1 to heat the thermistor to a temperature of about twenty to thirty degrees Celsius above ambient. A reference thermistor 3 is attached to conduit 1 to measure the temperature of the gas flowing in conduit 1.

Thermistors 2 and 3 are electrically connected to the inputs 6 and 7 of a differential amplifier 5 which generates an output voltage at terminal 8 which is related to the voltage difference at its inputs as is well known in the art. Offset potentiometer 9 is used to adjust the voltage at output 8 to zero volts when the flow in conduit 1 is zero to adjust for the temperature of gas conduit 1. In operation, gas flow in conduit 1 cools thermistor 2 thereby raising its resistance and increasing the voltage at terminal 8 which, therefore, is directly related to the flow rate in conduit 1.

Referring to FIG. 2, module 14 includes a microprocessor 32 which is operatively connected to read-only memory (ROM) 34 and random access memory (RAM) 36 as is well known in the art. The electrical signals from sensors 28 and 30 are applied to microprocessor 32 via lines 38 and 40 so that the flow rate and oxygen concentration of the oxygen-enriched air in line 22 can be periodically stored in RAM 36 as discussed hereafter. A modem 42 is connected to microprocessor 32 to permit the data stored in RAM 36 to be periodically formatted and transmitted over conventional telephone line 20 to remote computer 18 as discussed hereafter. The microprocessor 32 also includes a real time clock function that permits a determination of the length of a session of oxygen therapy along with the current time and date.

Figure 3:
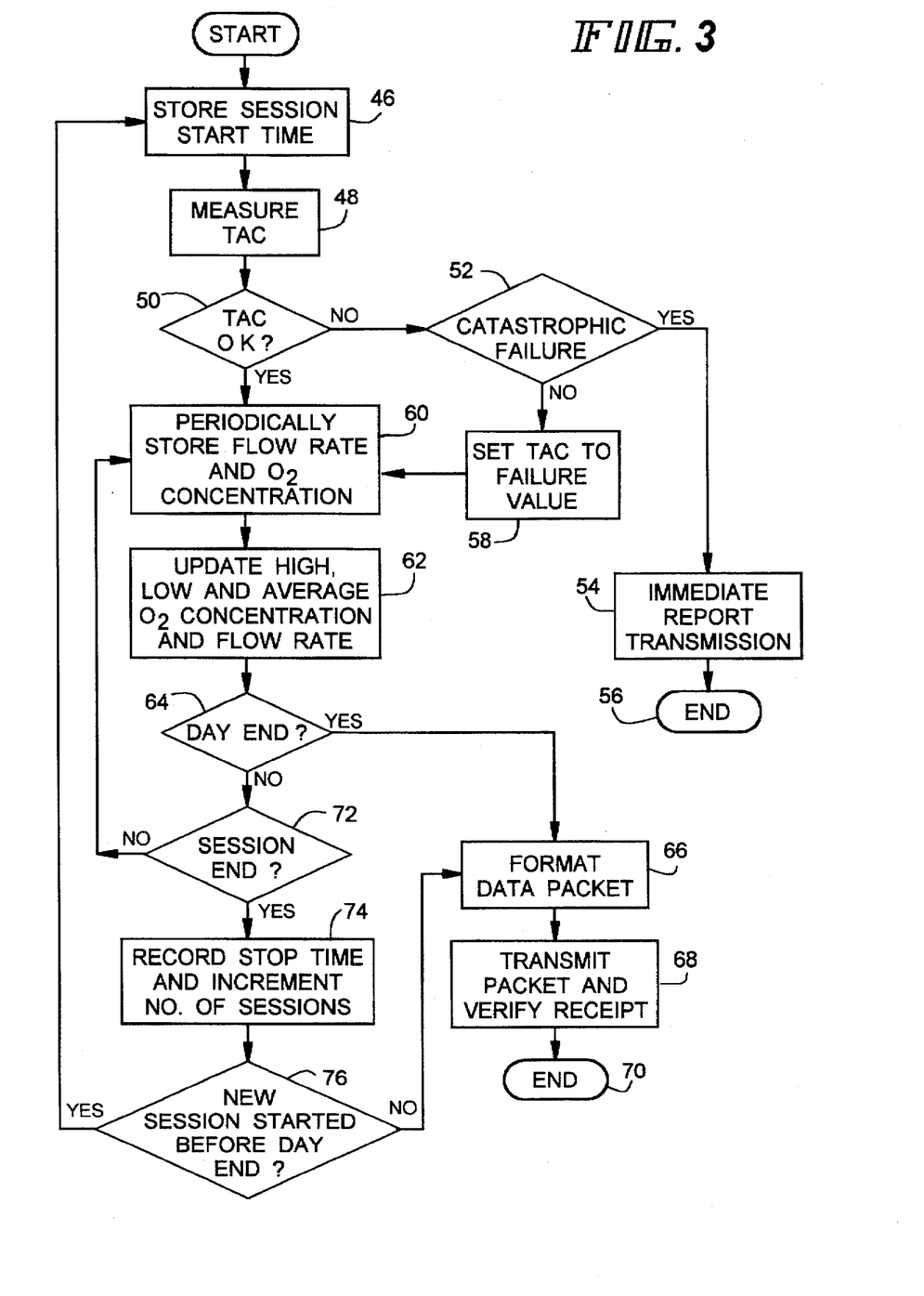
FIG. 3 is a flow diagram illustrating the program steps followed by the module of FIG. 1 to store and format the data to be transmitted to the remote computer.

FIG. 3 is a flow diagram illustrating the program steps that module 14 follows to periodically format and transmit a data packet (FIG. 4) to remote computer 18. The steps shown in FIG. 3 are stored as a computer program in ROM 34 and are executed by the microprocessor 32. It should be understood by those skilled in the art that different hardware systems use different computer code. The flow diagram of FIG. 3, however, permits the programming of invention on any system desired.

In general, information regarding the performance and use of oxygen concentrator 10 (or other oxygen delivery apparatus) by a patient is stored in a session format such that the length of time that oxygen-enriched air is supplied to a patient is measured. The flow rate and oxygen concentration of the oxygen-enriched air delivered to a patient is periodically stored in RAM 36 from the time when concentrator 10 is turned on to when concentrator 10 is turned off. During this time, high, low and average oxygen concentration and flow rate values are updated each time that the signals from sensors 28 and 30 are read, typically every six minutes. The start and stop time of each session also is stored in RAM 36.

At the beginning of each session, the time to an acceptable concentration of oxygen, or TAC value, is measured. For the TAC value to be acceptable, an oxygen concentration level of at least 85% must be continuously produced for at least fifteen minutes. The oxygen concentration, flow rate and other information stored in RAM 36 is periodically transmitted, preferably daily, to remote computer 18 as hereinafter discussed with reference to FIG. 3.

Figure 4:
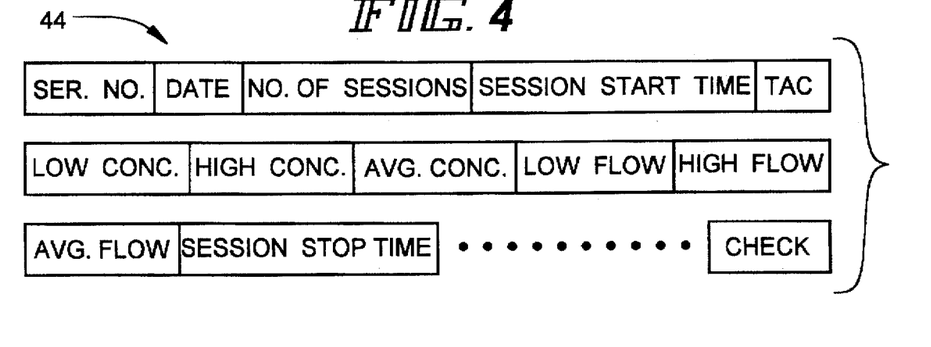
FIG. 4 is a block diagram of a data packet that is transmitted from the module of FIG. 1.

FIG. 4 illustrates a typical data packet 44 that is periodically transmitted from module 14 to remote computer 18. The data packet 44 contains a predetermined array of bytes and includes a header having a module identification code to permit remote computer 18 to identify module 14, the date and the number of sessions that occurred on that date. The remaining portions of the data packet are the following: the session start time; TAC value; low, high and average oxygen concentration and flow rate; session stop time and a check sum byte. This information is repeated in the data packet for each session.

A plurality of extra bytes can be provided at the end of a data packet so that additional information can be transmitted. For example, if a blood oximeter is used during an oxygen therapy session, then the blood gas information is placed at the end of the data packet for that session. Also, the level of liquid oxygen stored in a liquid oxygen delivery system and a low battery warning can be included.

A detailed explanation of how the module generates each data packet is presented with reference to FIG. 3. A start time is stored at the beginning of a session when oxygen-enriched air is delivered to a patient. A TAC value is also measured, steps 46–48. If the TAC value is not acceptable and a catastrophic failure has occurred, then the program ends after immediately transmitting a failure report to remote computer 18, steps 50–54. A catastrophic failure occurs when less than about 70 percent oxygen-enriched air is delivered to a patient. However, if an insufficient (but not catastrophic) oxygen concentration percentage is being delivered, then the TAC value is set to a predetermined failure value, step 58.

The flow rate and oxygen concentration of the enriched air delivered to a patient is periodically stored and high, low and average oxygen concentrations are updated, steps 60–62. At the end of a predetermined interval, preferably daily, the information stored in RAM 36 is formatted into a data packet (FIG. 4) and transmitted to remote computer 18 with the program then ending, steps 68–70. If the day is not over and the session has not ended, then the periodic storing of the flow rate and oxygen concentration is continued, step 64 and 72. When a session is completed before the end of a day, the session stop time is stored and the number of sessions is incremented, step 74. The program returns to step 46 if a new session is started before the day ends, step 76.

A unique feature of the present invention is that any number of patients in a given area who use oxygen concentrators (or other oxygen delivery apparatus) can be easily monitored by remote computer 18 by providing each concentrator with a sensing and communications module as described above. Preferably, remote computer 18 is centrally located among the patients so that service calls thereto can be minimized and made as efficiently as possible.

Figure 5:
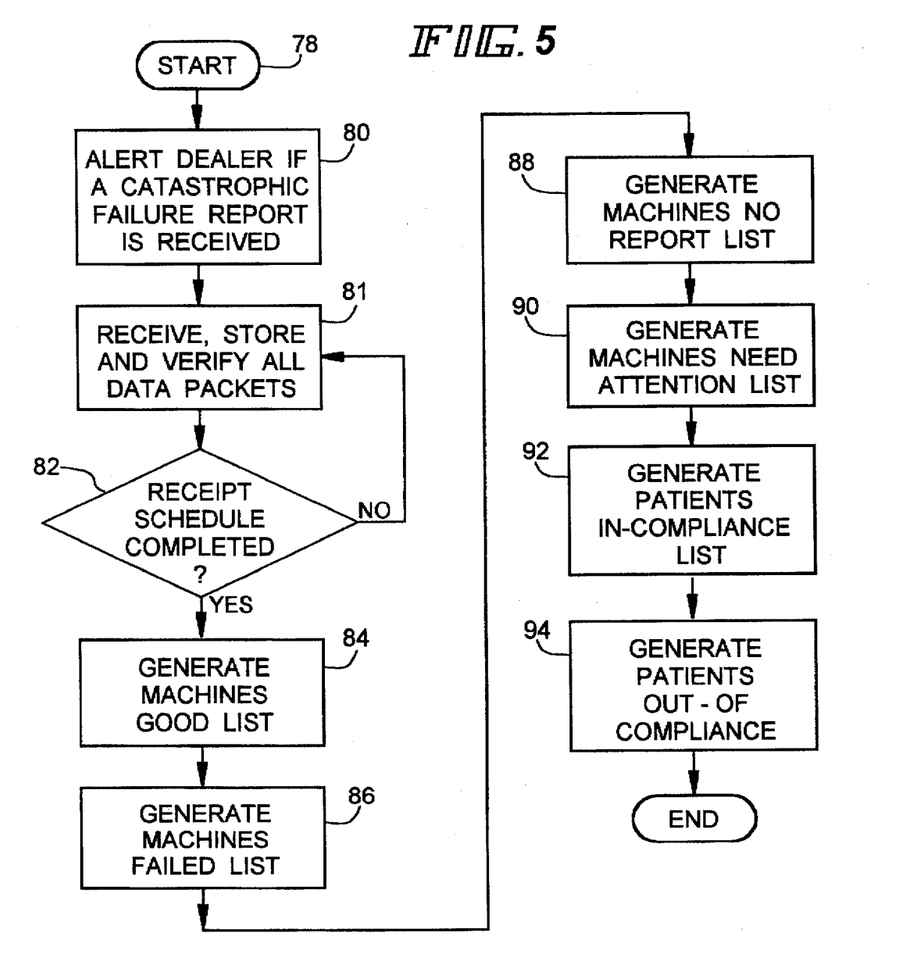
FIG. 5 is a flow chart illustrating the program steps necessary to determine patient compliance with a prescribed regimen of use and operational status information of an oxygen concentrator.

FIG. 5 is a flow diagram illustrating the program steps that remote computer 18 follows to determine the operational status of each of the oxygen concentrators (or other oxygen delivery apparatus) and whether each patient is using their oxygen concentrator in the manner prescribed. The steps shown in FIG. 5 are stored as a database computer program in a read only memory associated with the remote computer and permit the programming of the invention on any type of hardware system desired.

Whenever the remote computer receives notice that a catastrophic failure has occurred, the database program immediately prints a notice to that effect, steps 78 and 80. For each reporting period, preferably daily, the data packets transmitted from all of the sensing and communications modules in use in the area associated with the remote computer are received and verified according to a random schedule, steps 80–82. If a module does not report to the base computer on schedule, then it is recognized that a communications error occurred with that module. The data packets are stored and added to the patient's file in a memory associated with the remote computer.

When the transmission schedule is completed, the database program applies a predetermined set of criteria to the data for all of the oxygen concentrators to allow the data to be grouped and reported. By analysis of the reported data, the operator can efficiently allocate service personnel by anticipating concentrator (or other oxygen delivery apparatus) failures and can determine whether a patient is using their oxygen concentrator in the manner prescribed. The database program arranges the stored data in two general ways: (1) information relating to the performance of the oxygen delivery apparatus and (2) information relating to patient compliance.

First, a "machines good" list is generated in which all of the oxygen concentrators that transmitted a data packet to the remote concentrator on schedule and that functioned normally over the reporting period are included, step 84. For example, the oxygen concentration supplied to the patient did not go below 85% during the reporting period for these machines. The next category is the "machines failed" list which includes all oxygen concentrators that produced an oxygen concentration of (1) less than 85% for more than twenty-five minutes during a reporting period, (2) below 70% at any time or (3) if the TAC exceeds thirty minutes, step 86.

Any module that did not transmit a data packet to the remote computer as scheduled are included in the "no report" list, step 88. Oxygen concentrators that produce oxygen concentrations above 85% but which are falling are included in the "machines need attention" list, step 90. This is essentially a predictive feature to identify machines which are functioning normally but which are showing indications of failure.

The second category organized by the database program, patients in-compliance and patients out-of-compliance lists are generated in steps 92–94. In general, each patient must follow through with a prescribed regimen of use of an oxygen concentrator. The patient must take a given flow rate of sufficiently oxygen-enriched air for a given period of time each day. Based upon the seriousness of the patient's medical conditions, variations from the oxygen prescriptions are allowed. To determine whether a patient is in compliance with prescribed uses, the database program compares the patient's actual use of the concentrator with the allowed variation of his prescription.

Figure 6A:
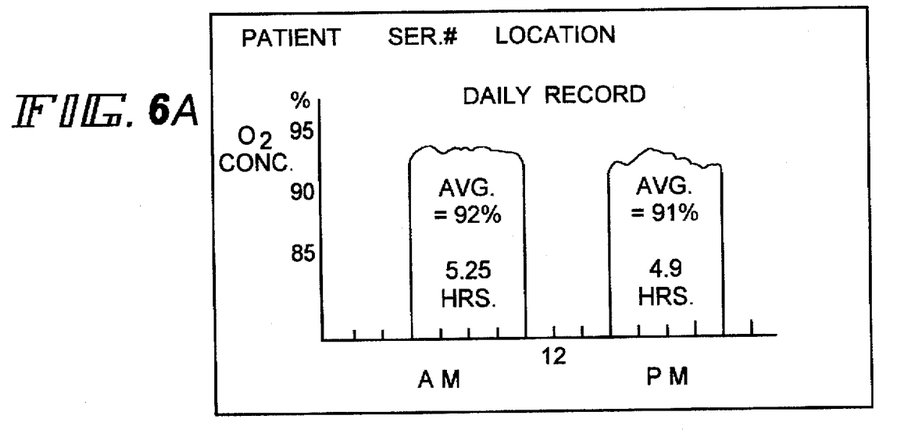
FIGS. 6A and 6B are graphs that show the operational history of an oxygen concentrator.
Figure 6B:
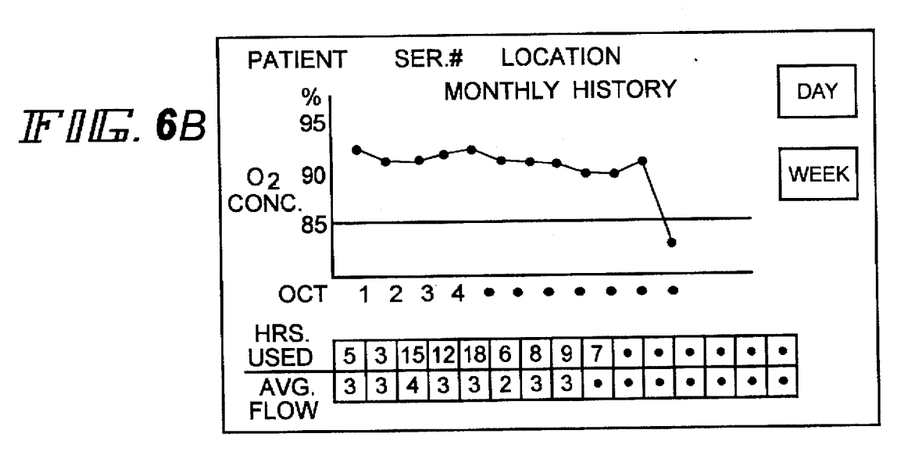

FIG. 6A is a graph that illustrates a typical oxygen concentrator (or other oxygen delivery apparatus) that is functioning normally and that has transmitted its data packet to the remote computer on schedule. FIG. 6B is a graph illustrating a failed machine that produced an average oxygen concentration below the acceptable level of eighty-five percent on a given day. These graphs can be presented in daily, weekly or monthly reporting formats so that the remote computer operator can review each concentrator's operating history over a desired period of time. Oxygen concentrations that have a decreasing oxygen concentration over time indicate that problems with the concentrator are developing and that the concentrator should be serviced so that a catastrophic failure will not take place. Well known statistical analysis techniques can be used for these purposes.

Figure 7:
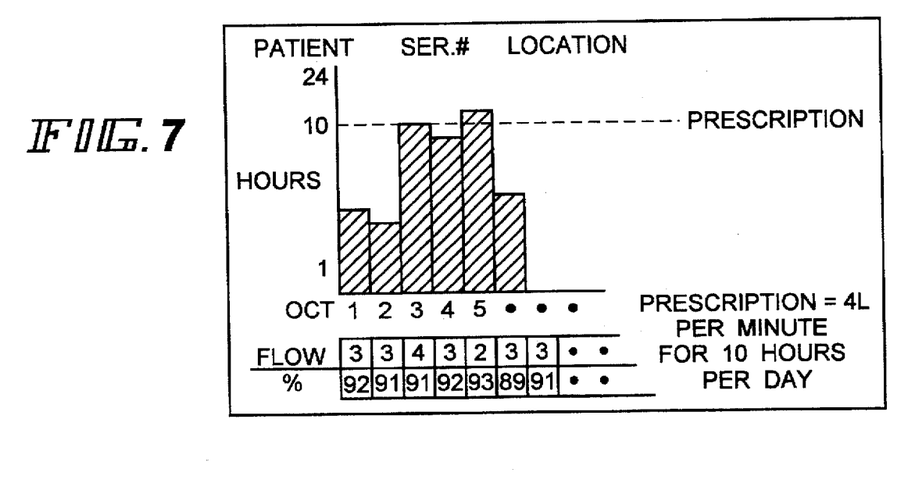
FIG. 7 is a graph that permits patient compliance with a prescribed regimen of use of an oxygen concentrator to be determined.

FIG. 7 is an example of a graph permitting patient compliance to be determined. This graph shows that the patient's prescription is to use the concentrator ten hours each day and to receive four liters per minute of oxygen-enriched air. The average flow rates and oxygen concentrations delivered on each day are listed below the graph for each day. By comparing the plot of the patient's prescription with the patient's actual use of the concentrator, it can be determined whether the patient is or is not in compliance for each reporting period with the oxygen prescription.

While the invention has been illustrated and described in detail in the drawings and the foregoing description, the same is to be considered as illustrative and not restrictive in character, it being understood that only the preferred embodiment has been shown and described and that all changes and modifications that come within the spirit of the invention are desired to be protected.

What is claimed is:

1. A sensing and communications system for use with an oxygen delivery apparatus which delivers oxygen-enriched air to a patient to permit remote compliance monitoring of said oxygen delivery apparatus, comprising:

a) means for measuring a session length during which said oxygen-enriched air is continuously supplied to said patient and measuring data related to the delivered flow rate of oxygen-enriched air from said oxygen delivery apparatus at one or more times during the measured session;

b) means for transmitting said measured delivered flow rate data and session length data to a remote location; and c) means, at said remote location, for storing information specifying a prescribed regimen of use for said patient including session length and delivered flow rate information, for receiving the transmitted data and comparing it to the prescribed session length and delivered flow rate information to determine patient and oxygen delivery apparatus compliance with the prescribed regimen of use.

2. The sensing and communications system of claim 1 wherein said measuring means includes a restricted orifice in circuit with said delivery apparatus and a sensor for generating a signal which is related to said flow rate by measuring the pressure drop across said orifice.

3. The sensing and communications system of claim 1 wherein said measuring means includes a conduit in circuit with said delivery apparatus and a sensor positioned therein for generating a signal which is related to said flow rate by measuring the temperature of said sensor.

4. The sensing and communications system of claim 1 wherein said measuring means includes clock means for measuring said session length.

5. The sensing and communications system of claim 4 wherein said flow rate and said session length data are periodically transmitted to said remote means, such data being stored in a memory prior to transmission.

6. The sensing and communications system of claim 5 wherein said measuring means further includes means for measuring data related to the oxygen concentration of said oxygen-enriched air supplied to said patient at one or more times during the measured session, such oxygen concentration data being stored in said memory and periodically transmitted to said remote means.

7. The sensing and communications system of claim 1 wherein said remote means includes means for displaying a comparison of said prescribed regimen with the transmitted data to provide an indication of whether the patient and oxygen delivery apparatus are complying with said prescribed regimen.

8. The sensing and communications system of claim 1 wherein said remote means includes a memory for storing the transmitted data for multiple sessions and means for determining whether said oxygen delivery apparatus is trending toward failure based on a comparison of current data with stored data.

9. The sensing and communications system of claim 1 wherein said oxygen delivery apparatus is a liquid delivery system.

10. The sensing and communications system of claim 1 wherein said oxygen delivery apparatus is an oxygen concentrator.

11. The sensing and communications system of claim 1 further comprising means for determining whether said oxygen delivery apparatus is in a failure condition and for generating a failure notice which is transmitted to said remote means.

12. A sensing and communications system for use with an oxygen delivery apparatus which delivers oxygen-enriched air to a patient to permit remote compliance monitoring of said oxygen delivery apparatus, comprising:
 a) means for measuring data related to the oxygen concentration and delivered flow rate of oxygen-enriched air continuously supplied to said patient during use of said oxygen delivery apparatus;
 b) means for periodically transmitting said oxygen concentration and delivered flow rate data to a remote location; and
 c) means, at said remote location, for receiving, storing and analyzing said periodically transmitted data to determine the current operational status of said oxygen delivery apparatus and for predicting whether said apparatus is trending toward failure based on a comparison of currently transmitted data with stored transmitted data.

13. The sensing and communications system of claim 12 wherein said measuring means includes a memory in which said delivered flow rate and oxygen concentration data are stored, said stored data being periodically transmitted to said remote means.

14. The sensing and communications system of claim 13 further including processor means for measuring a time to acceptable concentration (TAC), said TAC value being periodically stored in said memory and transmitted to said remote means.

15. The sensing and communications system of claim 13 wherein said means for measuring includes processor means for periodically determining high, low and average flow rates and oxygen concentrations of said oxygen-enriched air supplied to said patient, such data being stored in said memory and periodically transmitted to said remote means.

16. The sensing and communications system of claim 12 wherein said measuring means includes a restricted orifice in circuit with said delivery apparatus and a sensor for generating a signal which is related to said flow rate by measuring the pressure drop across said orifice.

17. The sensing and communications system of claim 12 wherein said measuring means includes a conduit in circuit with said delivering apparatus and a sensor positioned therein for generating a signal which is related to said flow rate by measuring the temperature of said sensor.

18. The sensing and communications system of claim 12 further comprising means for determining whether said oxygen delivery apparatus is in a failure condition and for generating a failure notice which is transmitted to said remote means.

19. The sensing and communications system of claim 12 wherein said oxygen delivery apparatus is an oxygen concentrator.

20. A sensing and communications system for use with a plurality of oxygen delivery apparatus each of which delivers oxygen-enriched air to a patient, comprising:
 a) a plurality of sensing and communications modules for use with said home oxygen delivery apparatus, each of said modules including:
  i) means for measuring a session length during which oxygen-enriched air is continuously supplied to said patient and measuring data related to the delivered flow rate and oxygen concentration of oxygen-enriched air from said oxygen delivery apparatus at one or more times during the session, and
  ii) means for periodically transmitting said flow rate, oxygen concentration and session length data to a remote location; and
 b) means, at said remote location, for storing for each oxygen delivery apparatus, patient information specifying a prescribed regimen of use including session length, delivered flow rate and oxygen concentration information, for receiving and storing the transmitted data and for:
  i) comparing the transmitted flow rate and session length data to prescribed flow rate and session length data to determine patient compliance with a prescribed regimen of use, and
  ii) analyzing said periodically transmitted flow rate and oxygen concentration data to determine both the current operational status of said oxygen delivery apparatus and for predicting whether said apparatus is trending toward failure based on a comparison of currently transmitted data with stored transmitted data.

21. A sensing and communications system for use with an oxygen delivery apparatus that delivers oxygen-enriched air to a patient to permit remote compliance monitoring of said oxygen delivery apparatus, comprising:

a) a clock for measuring a session length during which said oxygen-enriched air is continuously supplied to said patient and a flow sensor for measuring data related to the delivered flow rate of oxygen-enriched air from said oxygen delivery apparatus at one or more times during the session;

b) a transmitter for sending said delivered flow rate data and measured session length to a remote location; and c) a data processor at said remote location for storing information specifying a prescribed regimen of use for said patient including session length and flow rate information, for receiving the sensed flow rate data and measured session length and comparing it to the prescribed session length and flow rate information to determine patient and oxygen delivery apparatus compliance with the prescribed regimen of use.

22. The sensing and communications system of claim 21 wherein said flow sensor includes a restricted orifice in circuit with said delivery apparatus and a pressure sensitive device for generating a signal which is related to said flow rate by measuring the pressure drop across said orifice.

23. The sensing and communications system of claim 21 wherein said flow sensor includes a conduit in circuit with said delivery apparatus and a temperature sensitive device positioned therein for generating a signal which is related to said flow rate by measuring the temperature of oxygen-enriched air in the conduit.

24. The sensing and communications system of claim 21 wherein said clock includes a microprocessor clock means for measuring said session length.

25. The sensing and communications system of claim 24 wherein said flow rate and said session length data are periodically transmitted to said remote means, such data being stored in a memory prior to transmission.

26. The sensing and communications system of claim 25 further comprising an oxygen sensor for measuring data related to the oxygen concentration of said oxygen-enriched air supplied to said patient, such oxygen concentration data being stored in said memory and periodically transmitted to said remote means.

27. The sensing and communications system of claim 21 wherein said remote data processor includes means for displaying a comparison of said prescribed regimen with the transmitted data to provide an indication of whether the patient is complying with said prescribed regimen.

28. The sensing and communications system of claim 21 wherein said remote data processor includes a memory for storing the transmitted data and means for predicting whether said oxygen delivery apparatus is trending toward failure based on a comparison of current data with stored data.

29. The sensing and communications system of claim 21 wherein said oxygen delivery apparatus is a liquid delivery system.

30. The sensing and communications system of claim 21 wherein said oxygen delivery apparatus is an oxygen concentrator.

31. The sensing and communications system of claim 21 further comprising means for determining whether said oxygen delivery apparatus is in a failure condition and for generating a failure notice which is transmitted to said remote means.

32. A sensing and communications system for use with an oxygen delivery apparatus that delivers oxygen-enriched air to a patient to permit remote compliance monitoring of said oxygen delivery apparatus, comprising:

a) sensors for measuring data related to the delivered flow rate and oxygen concentration of oxygen-enriched air continuously supplied to said patient from said oxygen delivery apparatus;

b) a transmitter for periodically transmitting said delivered flow rate and oxygen concentration data to a remote location; and c) a computer at said remote location, for receiving, storing and analyzing said periodically transmitted data to determine the current operational status of said home oxygen delivery apparatus and to predict whether said apparatus is trending toward failure based on a comparison of currently transmitted data with stored transmitted data.

33. The sensing and communications system of claim 32 further including a memory in which said delivered flow rate and oxygen concentration data are stored, said stored data being periodically transmitted to said remote computer.

34. The sensing and communications system of claim 33 further including a processor for measuring a time to acceptable concentration (TAC), said TAC value being periodically stored in said memory and transmitted to said remote computer.

35. The sensing and communications system of claim 33 further including a processor for periodically determining high, low and average flow rates and oxygen concentrations of said oxygen-enriched air supplied to said patient, such data being stored in said memory and periodically transmitted to said remote computer.

36. The sensing and communications system of claim 32 wherein said sensors include a restricted orifice in circuit with said delivery apparatus and a pressure sensitive device for generating a signal which is related to said flow rate by measuring the pressure drop across said orifice.

37. The sensing and communications system of claim 32 wherein said sensors include a conduit in circuit with said delivery apparatus and a temperature sensitive device positioned therein for generating a signal which is related to said flow rate by measuring the temperature of said sensor.

38. The sensing and communications system of claim 32 further comprising a processor for determining whether said oxygen delivery apparatus is in a failure condition and for generating a failure notice which is transmitted to said remote means.

39. The sensing and communications system of claim 32 wherein said oxygen delivery apparatus is an oxygen concentrator.

40. A method for remote compliance monitoring of use of an oxygen delivery apparatus that delivers oxygen-enriched air to a patient, comprising:

a) measuring a session length during which said oxygen-enriched air is continuously supplied to said patient;

b) sensing data related to the delivered flow rate of oxygen-enriched air from said oxygen delivery apparatus at one or more times during the measured session;

c) transmitting said sensed flow rate data and measured session length to a remote location;

d) storing at said remote location information specifying a prescribed regimen of use for said patient including session length and flow rate information; and e) receiving at said remote location the sensed flow rate data and measured session length and comparing it to the prescribed session length and flow rate information to determine patient and oxygen delivery apparatus compliance with the prescribed regimen of use.

41. A method for remote compliance monitoring of use of an oxygen delivery apparatus that delivers oxygen-enriched air to a patient, comprising:
   a) measuring data related to the delivered flow rate and oxygen concentration of oxygen-enriched air continuously supplied to said patient from said oxygen delivery apparatus;
   b) periodically transmitting said delivered flow rate and oxygen concentration data to a remote location; and
   c) receiving, storing and analyzing in a computer at said remote location said periodically transmitted data to determine both the current operational status of said oxygen delivery apparatus and for predicting whether said apparatus is trending toward failure based on a comparison of currently transmitted data with stored transmitted data.

* * * * *